United States Patent [19]

Hsu et al.

[11] 4,387,471
[45] Jun. 14, 1983

[54] RETAINER FOR SURGEON'S EYE GLASSES

[76] Inventors: Herbert H. Hsu; Inri Tan-Hsu, both of 3745 Woodvale Rd., Birmingham, Ala. 35223

[21] Appl. No.: 264,570

[22] Filed: May 18, 1981

[51] Int. Cl.³ .......................... A61F 9/00; B32B 3/06; A61M 15/00
[52] U.S. Cl. ..................................... 2/10; 428/100; 2/DIG. 6; 128/201.12
[58] Field of Search ............... 2/10, DIG. 6, 202, 205; 428/100, 40, 99; 128/201.12, 201.15

[56] References Cited

U.S. PATENT DOCUMENTS

| 3,575,165 | 4/1971 | Heale | 128/100 X |
| 4,179,753 | 12/1979 | Aronberg et al. | 2/DIG. 11 |
| 4,312,338 | 1/1982 | Glassman | 128/201.12 |

Primary Examiner—Doris L. Troutman
Attorney, Agent, or Firm—Woodford R. Thompson, Jr.

[57] ABSTRACT

A retainer for a surgeon's eye glasses embodies a tape-like member with one end portion thereof extending around the nose bridge of the glasses and overlapping and detachably connected to an adjacent portion of the tape-like member. The other end portion of the tape-like member extends alongside and is detachably connected to a superjacent portion of a surgical hood.

2 Claims, 2 Drawing Figures

U.S. Patent  Jun. 14, 1983  4,387,471
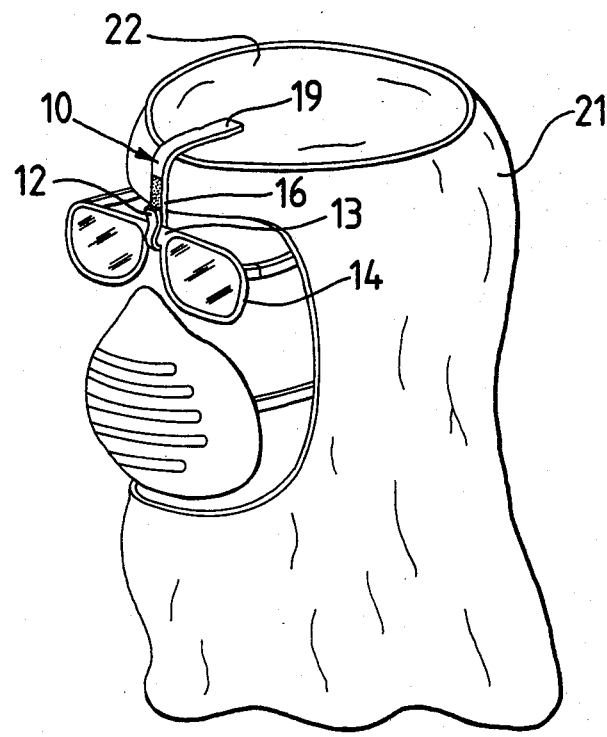
FIG. 1
FIG. 2
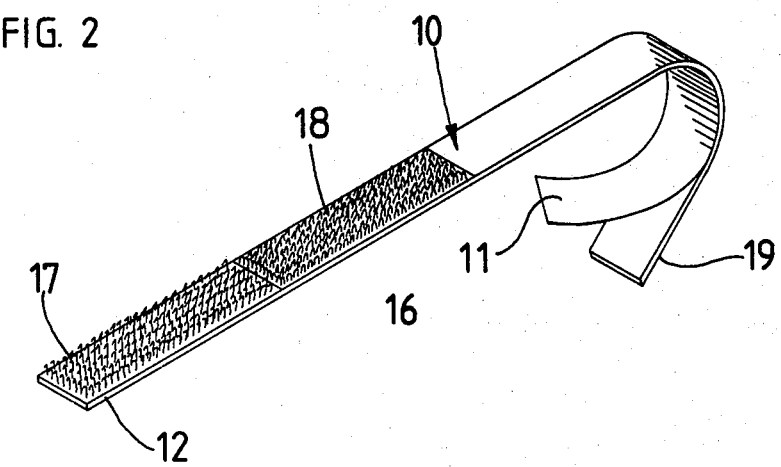

RETAINER FOR SURGEON'S EYE GLASSES

BACKGROUND OF THE INVENTION

This invention relates to a retainer for eye glasses and more particularly to a retainer which detachably connects a surgeon's glasses to a surgical hood.

Heretofore, surgeons wearing eye glasses have encountered difficulties in retaining their glasses in place during long hours of tedious surgery. This is especially true in view of the fact that it is often necessary to remove them during surgery without removing the surgical hood. In particular, when a surgeon wearing glasses performs tedious surgery, such as microsurgery, cardio-vascular surgery, emergency (trauma) surgery and the like, he must be able to keep his glasses from slipping due to perspiration or long moments of searching to locate a particular problem and at the same time he must be able to remove them and substitute therefor frames which carry special magnifying lenses. Heretofore, it has been the usual practice for the surgeon to tape the frame of the glasses to his nose and/or temple to keep them from slipping and then remove the tape, leaving the surgical hood in place, when he changes to a frame for supporting special magnifying lenses. Such taping is not only time consuming but is also very uncomfortable and troublesome to the surgeon. Also there is a chance that the surgeon might drop his glasses on the sterilized field or on the patient's open wound where it will cause infection to the patient and contaminate the sterilized field.

SUMMARY OF THE INVENTION

In accordance with our invention, we overcome the above and other difficulties by providing a retainer for glasses which is simple of construction and economical of manufacture. Our improved retainer retains a surgeon's glasses positively in place and at the same time permits quick and easy removal thereof without disturbing his operation and/or his surgical hood. Our retainer embodies a flexible tape-like member of a length for one end portion thereof to extend around the nose bridge of a surgeon's glasses and then overlap and be detachably connected to an adjacent portion of the tape-like member, with the other end portion of the tape-like member extending upwardly over a superjacent portion of a surgical hood. Adhesive means detachably secures the other end portion of the tape-like member to the hood.

DESCRIPTION OF THE DRAWINGS

A retainer device embodying features of our invention is illustrated in the accompanying drawing, forming part of this application, in which:

FIG. 1 is a perspective view showing our retainer detachably connecting the nose bridge of a pair of glasses to a superjacent portion of the surgical hood; and FIG. 2 is an enlarged perspective view showing our retainer removed from the glasses and surgical hood.

DETAILED DESCRIPTION

Referring now to the drawing for a better understanding of our invention, we show a flexible tape-like member 10 in the form of a conventional type pressure sensitive tape having an adhesive on one side thereof covered by a detachable connected backing strip 11. One end portion 12 of the tape-like member 10 is of a length to extend around the nose bridge 13 of a surgeon's glasses 14 and overlap an adjacent portion 16 of the tape-like member 10, as shown in FIG. 1. The end portion 12 and the adjacent portion 16 of the tape-like member 10 have cooperating surfaces facing each other, with one surface carrying a plurality of small hook-like members 17 in position to engage a felt-like material 18 carried by the other facing surface. Preferably, the hook-like members 17 are carried by the end 12 with the felt-like material 18 carried by the adjacent portion 16 as shown in FIG. 2. A conventional type fastening device embodying such hook-like members 17 and felt-like material 18 is sold under the trade name "VELCRO".

The tape-like member 10 is of a length for the other end portion 19 thereof to extend upwardly over a superjacent portion of a surgical hood indicated at 21. As shown in FIG. 2, the backing strip 11 covering the adhesive is at the opposite side of the pressure sensitive tape from the side thereof carrying the hook-like members 17 and the felt-like material 18 whereby the adhesive and backing strip 11 carried by the end portion 19 are at the side thereof adjacent the hood 21. Accordingly, after removal of the backing strip 11, the end portion 19 may be attached to the adjacent surface of the hood 21 by pressing the adhesive carrying side of the end portion 19 into contact with the hood. The backing strip 11 of the tape-like member 10 should be a little longer than the end portion 19 so that it will permit the surgeon and/or assistant to peel off the backing strip 11 quickly. In actual practice, we have found that by detachably connecting the end portion 19 to the top portion 22 of the surgical hood 21 in substantial alignment with the nose bridge of the surgeon's eye glasses is satisfactory in every respect for retaining the glasses in place. However, it will be apparent that the tape-like member 10 may be detachably connected to other portions of the surgical hood 21.

From the foregoing description the operation of our improved retainer for surgeon's eye glasses will be readily understood. First, the end portions 12 and 16 of the tape-like member 10 are wrapped around the nose bridge 13 of a surgeon's glasses 14 in position for the hook-like members 17 to engage the felt-like material 18 as shown in FIG. 1. Next, with the surgical hood 21 and the glasses 14 in place, the backing strip 11 is removed from the tape-like member 10 so that the end portion 19 carrying the adhesive may be attached to a superjacent portion of the surgical hood as shown. When the surgeon desires to remove the glasses 14 or change to a frame carrying special magnifying lenses, he disengages the end portion 12 from the adjacent portion 16 whereby the glasses 14 may be easily removed. The nose bridge of the frame carrying special lenses may then be attached between the end portions 12 and 16 as described above without disturbing the surgical hood.

From the foregoing decription, it will be seen that we have devised an improved retainer for surgeon's eye glasses which is simple of construction and economical to manufacture. Also, we provide an improved retainer which detachably connects the nose bride of a surgeon's eye glasses to a hood with a minimum of effort, thus permitting quick removal of the surgeon's eye glasses and quick replacement thereof by a frame carrying special surgical magnifying lenses without removal of the hood. Furthermore, our retainer secures the surgeon's eye glasses in place in a more comfortable and less troublesome manner than devices heretofore employed.

While we have shown our invention in but one form, it will be obvious to those skilled in the art that it is not so limited, but is susceptible of various changes and modifications without departing from the spirit thereof.

What we claim is:

1. In a retainer for detachably connecting a surgeon's eye glasses having a nose bridge to a surgical hood,
    (a) an elongated flexible tape-like member of a length for one end portion thereto to extend around said nose bridge and overlap an adjacent portion of said tape-like member with the other end portion of said tape-like member extending upwardly over a superjacent portion of said hood,
    (b) cooperating surfaces carried by said one end portion and said adjacent portion and adapted to face each other while said one end portion overlaps said adjacent portion with hook-like members carried by one of said cooperating surfaces in position to engage a felt-like material carried by the other of said cooperating surfaces to detachably connect said one end portion to said ajacent portion with said nose bridge secured therebetween, and
    (c) an area of adhesive carried by said other end portion of said tape-like member in position to detachably connect said other end portion to said superjacent portion of said hood with said tape-like member limiting downward movement of the glasses and retaining them in place.

2. A retainer as defined in claim 1 in which the other end portion of said elongated flexible tape-like member is a length of pressure sensitive tape having an adhesive at one side thereof covered by a backing strip with said adhesive being at the opposite side of said tape-like member from the side thereof carrying said hook-like members and said felt-like material so that said adhesive is in position to contact said superjacent portion of said hood upon removal of said backing strip.

* * * * *